US010420837B2

(12) United States Patent
Shishido et al.

(10) Patent No.: US 10,420,837 B2
(45) Date of Patent: Sep. 24, 2019

(54) VACCINE PHARMACEUTICAL COMPOSITION FOR TRANSDERMAL ADMINISTRATION

(71) Applicant: NITTO DENKO CORPORATION, Osaka (JP)

(72) Inventors: Takuya Shishido, Osaka (JP); Daisuke Asari, Osaka (JP); Kyohei Matsushita, Osaka (JP); Katsuyuki Okubo, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/514,868

(22) PCT Filed: Oct. 1, 2015

(86) PCT No.: PCT/JP2015/077921
§ 371 (c)(1),
(2) Date: Mar. 28, 2017

(87) PCT Pub. No.: WO2016/052698
PCT Pub. Date: Apr. 7, 2016

(65) Prior Publication Data

US 2017/0216431 A1 Aug. 3, 2017

(30) Foreign Application Priority Data

Oct. 2, 2014 (JP) ................................ 2014-204020

(51) Int. Cl.
*A61K 39/39* (2006.01)
*A61K 39/00* (2006.01)
*A61K 39/02* (2006.01)
*A61K 39/12* (2006.01)
*A61K 9/70* (2006.01)

(52) U.S. Cl.
CPC ................ *A61K 39/39* (2013.01); *A61K 9/70* (2013.01); *A61K 39/00* (2013.01); *A61K 39/0011* (2013.01); *A61K 39/02* (2013.01); *A61K 39/12* (2013.01); *A61K 2039/54* (2013.01); *A61K 2039/55572* (2013.01); *A61K 2039/575* (2013.01); *A61K 2039/70* (2013.01)

(58) Field of Classification Search
None
See application file for complete search history.

(56) References Cited

U.S. PATENT DOCUMENTS 5,368,860 A * 11/1994 Sunami ................ A61K 9/7061 424/443
6,368,599 B1 * 4/2002 Langermann .......... A61K 39/39 424/184.1
9,439,872 B2 * 9/2016 Matsushita ............ A61K 38/00
9,962,439 B2 * 5/2018 Matsushita ............ A61K 39/00
10,017,545 B2 * 7/2018 DeShong ............. A61K 39/095
10,071,051 B2 * 9/2018 Okubo ................. A61K 9/0014
10,071,155 B2 * 9/2018 Kiyotoh ................. A61K 39/39
10,076,491 B2 * 9/2018 Asari ................... A61K 9/0014
10,092,505 B2 * 10/2018 Asari ..................... A61K 47/02
10,092,642 B2 * 10/2018 Fukasaka ............... A61K 39/12
2004/0131625 A1 * 7/2004 Berthet ................ A61K 39/118 424/184.1
2005/0152919 A1 * 7/2005 Ward ................... A61K 39/165 424/212.1
2005/0281847 A1 * 12/2005 Berthet ................ A61K 39/118 424/263.1

(Continued)

FOREIGN PATENT DOCUMENTS

EP 2116256 A1 * 11/2009 ........... A61K 9/7053
EP 2762152 A1 8/2014

(Continued)

OTHER PUBLICATIONS

Karande et al, Annual Rev. Chem. Biomol., 2010, 1:175-201 (Year: 2010).*

(Continued)

*Primary Examiner* — Nita M. Minnifield
(74) *Attorney, Agent, or Firm* — Greenblum & Bernstein, P.L.C.

(57) ABSTRACT

The present invention provides a vaccine pharmaceutical composition for transdermal administration which is safe, usable as a prophylactic or therapeutic agent for cancer or infectious diseases, and capable of safely and effectively inducing a systemic immune response. It can be administered to a human or animal skin, the vaccine pharmaceutical composition including: a lipopolysaccharide or its salt, derived from at least one gram-negative bacterium such as *Serratia, Lelercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, as an immunostimulant; and at least one antigen, the vaccine pharmaceutical composition having a mass ratio between the immunostimulant and the antigen, the total mass of the immunostimulant/the total mass of the antigen, of 0.002 to 500.

17 Claims, No Drawings

(56) References Cited

U.S. PATENT DOCUMENTS

| | | | | |
|---|---|---|---|---|
| 2007/0243132 A1* | 10/2007 | Russell-Jones | A61K 9/0014 424/1.11 |
| 2009/0010998 A1* | 1/2009 | Marchitto | A61K 9/7084 424/449 |
| 2013/0266612 A1 | 10/2013 | Fukasaka et al. | |
| 2014/0220055 A1* | 8/2014 | Okubo | A61K 9/0014 424/185.1 |
| 2014/0220056 A1* | 8/2014 | Shishido | A61K 9/0014 424/185.1 |
| 2014/0220057 A1 | 8/2014 | Okubo et al. | |
| 2014/0220058 A1* | 8/2014 | Maeda | A61K 9/0014 424/185.1 |
| 2014/0220063 A1* | 8/2014 | Asari | A61K 9/0014 424/189.1 |
| 2014/0220100 A1* | 8/2014 | Okubo | A61K 39/0005 424/443 |
| 2014/0220105 A1* | 8/2014 | Maeda | A61K 9/7023 424/449 |
| 2014/0234377 A1* | 8/2014 | Okazaki | A61K 39/0011 424/277.1 |
| 2016/0193327 A1* | 7/2016 | Fukasaka | A61K 39/12 424/196.11 |
| 2016/0213773 A1* | 7/2016 | Fukasaka | A61K 39/39 |
| 2016/0228540 A1* | 8/2016 | Kiyotoh | A61K 39/39 |
| 2016/0287697 A1* | 10/2016 | Matsushita | A61K 39/00 |
| 2017/0216429 A1* | 8/2017 | Shishido | A61K 39/00 |
| 2017/0216431 A1* | 8/2017 | Shishido | A61K 39/00 |
| 2017/0246287 A1* | 8/2017 | Shishido | A61K 9/0014 |
| 2017/0360908 A1* | 12/2017 | Shishido | A61K 38/00 |
| 2018/0147235 A1* | 5/2018 | Matsushita | A61K 39/02 |
| 2018/0169227 A1* | 6/2018 | Matsushita | A61K 39/00 |
| 2018/0326041 A1* | 11/2018 | Shishido | A61K 39/145 |

FOREIGN PATENT DOCUMENTS

| | | | | |
|---|---|---|---|---|
| EP | 2762154 A2 | 8/2014 | |
| JP | 2009-242367 | 10/2009 | |
| JP | 2013-231026 A | 11/2013 | |
| JP | 2014-169274 A | 9/2014 | |
| JP | 2014-169276 A | 9/2014 | |
| WO | WO-2007070983 A1 * | 6/2007 | A61K 9/0014 |
| WO | WO-2015050178 A1 * | 4/2015 | A61K 39/39 |
| WO | WO-2015050179 A1 * | 4/2015 | A61K 39/39 |
| WO | WO-2015050180 A1 * | 4/2015 | A61K 39/12 |
| WO | WO-2015050181 A1 * | 4/2015 | A61K 39/00 |
| WO | WO-2016052698 A1 * | 4/2016 | A61K 39/00 |
| WO | WO-2016178410 A1 * | 11/2016 | A61K 39/02 |

OTHER PUBLICATIONS

Lee et al, Vaccine, 2011, 29:8293-8301. available online: Sep. 3, 2011 (Year: 2011).*

Opal et al, Journal Infectious Diseases, Dec. 15, 2005, 192:2074-2080. electronically published Nov. 10, 2005 (Year: 2005).*

Taniguchi et al, Anticancer Research, 2006, 26:3997-4002 (Year: 2006).*

Fukasaka et al, PLoS One,2015, 10(5):e0126849. published: May 15, 2015 (Year: 2015).*

Pastore et al, Vritish J. Pharmacology, 2015, 172:2179-2209 (Year: 2015).*

InvivoGen, 2011, Vaccine Adjuvants 3 pages (Year: 2011).*

Namjoshi et al, New Approaches to Vaccine Research, 2011, 37/661(2). 18 pages (Year: 2011).*

Suh et al, Clinical Exp. Vaccine Res., 2014, 3:42-49 (Year: 2014).*

Arenas, Endocrine Metabolic and Immune Disorders—Drug Targets, 2012, 12:221-235 (Year: 2012).*

Hirobe et al., "Clinical study of transcutaneous vaccination using a hydrogel patch for tetanus and diphtheria", Vaccine, 2012, pp. 1847-1854, vol. 30, No. 10. In English.

Matsuo, "Development of Transcutaneous Vaccination System for Infectious Disease Countermeasure", Yakugaku Zasshi, 2012, pp. 1443-1450, vol. 132, No. 12. Partial translation and abstract provided.

Skountzou et al., "Transcutaneous immunization with inactivated influenza virus induces protective immune responses", Vaccine, 2006, pp. 6110-6119, vol. 24, No. 35-36. In English.

Nishizawa et al., "Homeostasis as Regulated by Activated Macrophage. I. Lipopolysaccharide (LPS) from Wheat Flour: Isolation, Purification and Some Biological Activities", Chemical and Parmaceutical Bulletin , 1992, pp. 479-483, vol. 40, No. 2. In English.

Okutomi et al., "Homestasis as regulated by activated macrophage, IV. Analgesic effect of LPSw, a lipopolysaccharide of wheat flour", Chemical and Pharmaceutical Bulletin, 1992, pp. 1001-1003, vol. 40, No. 4. In English.

Mizuno et al., "Oral or percutaneous administration of lipoplysaccharide of small molecular size may cure various intractable diseases: a new version of Coley's toxin", Molecular Biotherapy, 1992, pp. 166-169, vol. 4, No. 4. In English.

Hebishima et al., "Oral administration of immunopotentiator from Pantoea agglomerans 1 (IP-PA1) improves the survival of B16 melanoma-inoculated model mice", Experimental Animals, 2011, pp. 101-109, vol. 60, No. 2. In English.

Klechevsky et al., "Functional specializations of human epidermal Langerhans cells and CD14+ dermal dendritic cells", Immunity, 2008, pp. 497-510, vol. 29, No. 3. In English.

El-Ghorr et al., "Transcutaneous immunisation with herpes simplex virus stimulates immunity in mice", FEMS Immunology and Medical Microbiology, 2000, pp. 255-261, vol. 29, No. 4. In English.

International Search Report issued with respect to Application No. PCT/JP2015/077921, dated Nov. 24, 2015.

International Preliminary Report on Patentability issued with respect to Application No. PCT/JP2015/077921, dated Apr. 4, 2017.

Extended European Search Report for EP Application No. 15846575.7 dated Mar. 23, 2018.

Sang-Moo Kang et al., "Microneedle and mucosal delivery of influenza vaccines," Expert Rev. Vaccines, (2014) 11(5):547-560.

Dimitrios G. Koutsonanos et al., "Transdermal influenza immunization with vaccine-coated microneedle arrays," PLOS ONE (2009) 4(3):e4773.

Kevin E. Knockenhauer et al., "Protective antigen composite nanofibers as a transdermal anthrax vaccine," Engineering in Medicine and Biology Society and 30th Annual International Conference of the IEEE in Piscataway, NJ, Aug. 20, 2008.

Masahiro Fukasaka et al., "A lipopolysaccharide from Panteoa agglomerans is a promising adjuvant for sublingual vaccines to induce systemic and mucosal immune responses in mice via TLR4 pathway," PLOS ONE (May 15, 2015) 10(5):e0126849.

Office Action dated Jul. 9, 2019 in corresponding Japanese Application No. 2015-195689.

Mark T. Orr et al. "MyD88 and TRIF synergistic interaction is required for Th1-cell polarization with a synthetic TLR4 agonist adjuvant," European J. Of Immunology (2013), vol. 43, pp. 2398-2408.

* cited by examiner

VACCINE PHARMACEUTICAL COMPOSITION FOR TRANSDERMAL ADMINISTRATION

TECHNICAL FIELD

The present invention relates to a vaccine pharmaceutical composition for transdermal administration which is useful as a prophylactic or therapeutic agent for cancer or infectious diseases. In particular, the present invention relates to a vaccine pharmaceutical composition which contains a specific lipopolysaccharide as an immunostimulant together with an antigen and is capable of safely and effectively inducing a systemic immune response by transdermal administration thereof.

BACKGROUND ART

Common widely used vaccines are made from pathogens (e.g., microorganisms, viruses) or such pathogens whose toxicity is partially weakened or eliminated. The vaccines are administered to living bodies to induce immunity to prevent infectious diseases. Most of the vaccine formulations commercialized at present are injection products.

Injections, such as subcutaneous injection, intradermal injection, and intramuscular injection, are commonly used in administration of a vaccine for induction of immunity. In particular, since microorganisms or viruses cannot enter the body through the skin due to their sizes, invasive administration of a vaccine into the body is needed.

Injections, however, have problems of psychological burdens on patients, such as pain, fear, needle marks and scarring thereof, and the burden of visiting the hospital in their daily lives in a case where repeated administration is required. Additionally, injections further have problems that only medical practitioners can give them, that the intradermal injection which gives a high immune effect requires a proficient skill to give, that medical professionals are exposed to a risk of infection due to needle pricking, and that medical waste which necessitates special disposition, such as injection needles, is generated. Injection is therefore not necessarily the best administration route.

To overcome the situation, vaccination through the mucosa has attracted attention and mucosal administration (transnasal administration and oral administration)-type vaccines containing influenza virus as an antigen have been developed. For example, Patent Literature 1 discloses a case where immunity can be induced by transnasaly administering a *Pantoea* bacterium-derived lipopolysaccharide as an immunostimulant together with an antigen. According to Patent Literature 2, oral administration of a vaccine containing a *Pantoea* bacterium-derived lipopolysaccharide sufficiently induces an immune response.

However, it is highly possible that administration of an antigen through nasal mucosa gives severe side effects such as acute encephalopathy, though it gives a high effect. In addition, transnasal administration itself is complicated and difficult in the case where the administration subject is an elderly person or a baby. Moreover, physical factors such as snivel may inhibit stable exertion of the effect.

Whether or not immunity can be induced by transdermal administration of a vaccine containing a *Pantoea* bacterium-derived lipopolysaccharide has not been disclosed, and the dosage form appropriate for transdermal immunization has not been disclosed.

CITATION LIST

Patent Literature

Patent Literature 1: JP 2009-242367 A
Patent Literature 2: JP 2013-231026 A

SUMMARY OF INVENTION

Technical Problem

The present invention aims to, in consideration of the state of the art, provide a vaccine pharmaceutical composition for transdermal administration which is safe, usable as a prophylactic or therapeutic agent for cancer or infectious diseases, and capable of safely and effectively inducing a systemic immune response.

Solution to Problem

As a result of intensive studies to solve the above problem, the present inventors have found out that the systemic immune response can be safely and effectively induced by transdermal administration of a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus Methanosarcina, Clostridium, Micrococcus, Flavobacterium, Pantoea, Acetobacter, Zymomonas, Xanthomonas*, and *Enterobacter*, or its salt as an immunostimulant together with an antigen. The present invention was thus completed.

The present invention relates to a vaccine pharmaceutical composition for transdermal administration to be administered to a human or animal skin, the vaccine pharmaceutical composition including: a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, or its salt as an immunostimulant; and at least one antigen, the vaccine pharmaceutical composition having a mass ratio between the immunostimulant and the antigen, the total mass of the immunostimulant/the total mass of the antigen, of 0.002 to 500.

The vaccine pharmaceutical composition for transdermal administration of the present invention preferably has a dosage form of a patch.

The patch preferably includes a support and an adhesive layer containing an adhesive, and the adhesive preferably contains a hydrophilic base material.

The vaccine pharmaceutical composition for transdermal administration of the present invention is preferably used for inducing humoral immunity.

The vaccine pharmaceutical composition for transdermal administration of the present invention is preferably used for preventing an infectious disease.

The vaccine pharmaceutical composition for transdermal administration of the present invention is preferably used for preventing or treating cancer.

The antigen is preferably at least one of an infectious disease-derived antigen and a cancer antigen.

The present invention is specifically described in the following.

The vaccine pharmaceutical composition for transdermal administration of the present invention contains at least one antigen.

The antigen refers to all of the substances that can be a target of the immune response generated in a subject living body, and is preferably an infectious disease-derived antigen and/or a cancer antigen.

The infectious disease-derived antigen may also be a target of the immune response (e.g., mature of immunocompetent cells, increase in cytokine production, promotion of antibody production) upon contact with immunocompetent cells.

The vaccine pharmaceutical composition for transdermal administration containing the infectious disease-derived antigen is preferably used for preventing infectious diseases by preliminarily forming an antibody in a target living body. The vaccine pharmaceutical composition for transdermal administration of the present invention is suitably used for activating the humoral immunity.

The infectious disease-derived antigen used in the present invention is not limited as long as it is an infectious pathogen or an infectious pathogen-derived antigen.

The disease due to the infectious pathogen is not limited, and examples thereof include: virus diseases caused by infection with viruses such as adenovirus (e.g., human adenovirus), herpesvirus (e.g., herpes simplex virus (HSV-I, HSV-II), varicella-zoster virus (CMV), cytomegalovirus (VZV), human herpesvirus, or Kaposi sarcoma-associated herpesvirus), pox virus (e.g., smallpox virus, vaccinia virus, or orthopoxvirus such as molluscum contagiosum virus), picornavirus (e.g., polio virus, common cold virus, hepatitis A virus, rhinovirus, or enterovirus), orthomyxovirus (e.g., influenza virus), paramyxovirus (e.g., parainfluenza virus, mumps virus, measles virus, respiratory syncytial virus (RSV), or Newcastle disease virus), coronavirus (e.g., SARS coronavirus), papovavirus (e.g., human papillomavirus such as those causing genital warts, common warts, or plantar warts), parvovirus (e.g., adeno associated virus), togavirus (e.g., rubella virus), hepadnavirus (e.g., hepatitis B virus), flavivirus (e.g., Japanese encephalitis virus, yellow fever virus, dengue virus, West Nile fever virus, St. Louis encephalitis virus, Murray Valley encephalitis virus, hepatitis C virus, or hepatitis G virus), Hepevirus (e.g., hepatitis E virus), calicivirus (e.g., Norovirus), rhabdovirus (e.g., rabies virus or vesicular stomatitis virus), filovirus (e.g., Ebola hemorrhagic fever virus), arenavirus (e.g., Lassa virus or hepatitis D virus), bunyavirus (e.g., California encephalitis virus or Rift Valley fever virus), reovirus (e.g., rotavirus), or retrovirus (e.g., lentivirus such as human immunodeficiency virus (HIV) or adult T-cell leukemia virus); bacterial diseases such as those caused by infection with a bacterium such as *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*; fungous diseases such as Chlamydia, candidiasis, aspergillosis, histoplasmosis, and cryptococcal meningitis; malaria; Pneumocystis carinii pneumonia; leishmaniasis; cryptosporidiosis; toxoplasmosis; and Trypanosoma infection.

In the present invention, the infectious disease-derived antigen is preferably at least one selected from the group consisting of an influenza virus-derived antigen, a human papillomavirus-derived antigen, and a pneumococcus-derived antigen. In particular, an influenza virus-derived antigen is more preferred.

Here, the influenza virus is an RNA envelope virus belonging to Orthomyxoviridae, and having a particle size of about 100 nm in diameter, and is classified into types A, B and C based on the antigenicity of the internal protein. The influenza virus is composed of a core of ribonucleic acid (RNA) associated with an internal nucleocapsid surrounded by a virus envelope having a lipid bilayer structure or nucleic protein, and an external glycoprotein. The inner layer of the virus envelope is mainly formed of matrix protein, and the outer layer is mostly formed of a lipid substance derived from the host. RNA of the influenza virus has a multipartite structure. Influenza that is pandemic is caused by an influenza A virus, and the influenza A virus has two envelope glycoproteins: hemagglutinin (HA) and neuraminidase (NA), and is classified into 16 subtypes for HA and 9 subtypes for NA depending on the antigenicity.

In the present invention, as the infectious disease-derived antigen, an influenza A virus-derived antigen and an influenza B virus-derived antigen are preferably used. The subtype of the influenza A and B viruses is not particularly limited, and may be a subtype that is already isolated, or a subtype that will be isolated in future.

In the present invention, the influenza virus-derived antigen is not limited as long as it is at least a part of various components constituting the influenza virus, and may be a subvirion obtained by digesting a purified viral particle with an organic solvent and a surfactant or another reagent so that the lipid envelope is solubilized, or a viral subunit such as HA and NA, or may be a viral whole particle. From the view point of immunogenicity, HA or a viral whole particle is preferred. The viral whole particle is preferably inactivated with formalin or the like.

The method for preparing the aforementioned influenza virus antigen is not limited, and any known method can be used without restriction. One exemplary method includes: infecting a chicken egg with a viral strain that is isolated from an animal or a patient infected with influenza, culturing the chicken egg by an ordinary method, and preparing an antigen from the purified undiluted viral culture. Also an antigen derived from a virus prepared in cultured cells by genetic engineering may be used.

As used herein, the term “pharmacologically acceptable salt” refers to a salt that does not have an adverse effect on the administration subject and does not eliminate the pharmacological activity of components of the vaccine pharmaceutical composition. Examples thereof include inorganic acid salts (e.g., hydrochloride, phosphate), organic acid salts (e.g., acetate, phthalate, TFA salt), metal salts such as alkali metal salts (e.g., sodium salt, potassium salt), alkaline earth metal salts (e.g., calcium salt, magnesium salt) and aluminum salt, and amine salts (e.g., triethylamine salt, benzylamine salt, diethanolamine salt, t-butylamine salt, dicyclohexylamine salt, arginine salt, dimethyl ammonium salt, ammonium salt).

In the vaccine pharmaceutical composition for transdermal administration of the present invention, the antigen is required to be contained in an effective amount. For example, the antigen is preferably in an amount in the range of 0.01 to 10000 μg per single dose for a single object in the vaccine pharmaceutical composition for transdermal administration of the present invention. If the amount is less than 0.01 μg, the function as a prophylactic or therapeutic agent for infectious diseases or cancer may be insufficient. If the amount is more than 10000 μg, a safety problem may arise. The lower limit of the antigen content is more preferably 0.1 μg, and the upper limit thereof is more preferably 5000 μg.

The phrase "the mass of the antigen" as used herein refers to the mass of an antigen protein contained in the antigen in the vaccine composition, unless otherwise specified. When the antigen is a vivo-derived substance such as viruses, "the mass of the antigen" means the mass of all the proteins contained in the antigen.

The term "single object" as used herein may refer to any mammal, and is preferably a human.

The vaccine pharmaceutical composition for transdermal administration of the present invention contains an immunostimulant.

The term "immunostimulant" as used herein refers to any substance that assists, enhances, or improves the action of the antigen administered together, and may also be referred to as an "adjuvant".

The immunostimulant may be a toll-like receptor 4 (TLR4) agonist. In the present invention, as the toll-like receptor 4 (TLR4) agonist, a specific lipopolysaccharide, or a derivative or a salt thereof is used.

The "lipopolysaccharide (hereafter, also referred to as LPS)" as used herein may be a lipopolysaccharide itself or a derivative thereof as long as it has properties of the lipopolysaccharide. The salt as used herein may be any organic acid salt or inorganic acid salt, and is preferably a pharmacologically acceptable salt.

The LPS is a composite compound composed of a lipid and a saccharide existing in the outer membrane surrounding peptide glycan of cell walls of gram-negative bacteria such as *Escherichia coli, Salmonella typhimurium*, and *Bordetella pertussis*, and is known as an active component of O antigen and endotoxin [J. M. Ghuysen and R. Hakenbeck ed., "New Comprehensive Biochemistry", Vol. 27, Bacterial Cell Wall, p. 18, Elsevea, 1994].

The basic structure of the LPS consists of three components: lipid A having a specific lipid, an oligosaccharide covalently bonded thereto, which is called an R core, and an O-specific polysaccharide ("Nikkei Biotechnology Up-to-date Glossary", P. 431, Nikkei Macgraw-hill, 1985).

The structure of the O-specific polysaccharide is the most diverse in the components, specific for the bacterial species, and shows the activity as a so-called O antigen. Generally, it is characterized by a structure in which oligosaccharides made up of several kinds of monosaccharides are repeated. In addition, the one composed of identical monosaccharides, and the one not having a repetitive structure are also known.

The vaccine pharmaceutical composition for transdermal administration of the present invention contains a lipopolysaccharide derived from a specific gram-negative bacterium or its salt as the immunostimulant. Such a gram-negative bacterium or its salt is contained in many food items and herbal medicines, and hence assured to be safe to the living body, and extracts derived therefrom or modified substances thereof can also be used as they are.

Examples of bacteria from which a lipopolysaccharide for use in the immunostimulant is derived include *Serratia* (species closely related to *Pantoea*/bread, meat, milk, one species of indigenous bacteria), *Leclercia* (species closely related to *Pantoea*/food in general (soil bacteria)), *Rahnella* (species closely related to *Pantoea*/one species of indigenous bacteria), *Acidicaldus* (acetic bacteria/fermented food production), *Acidiphilium* (acetic bacteria/fermented food production), *Acidisphaera* (acetic bacteria/fermented food production), *Acidocella* (acetic bacteria/fermented food production), *Acidomonas* (acetic bacteria/fermented food production), *Asaia* (acetic bacteria/fermented food production), *Belnapia* (acetic bacteria/fermented food production), *Craurococcus* (acetic bacteria/fermented food production), *Gluconacetobacter* (acetic bacteria/fermented food production), *Gluconobacter* (acetic bacteria/fermented food production), *Kozakia* (acetic bacteria/fermented food production), *Leahibacter* (acetic bacteria/fermented food production), *Muricoccus* (acetic bacteria/fermented food production), *Neoasaia* (acetic bacteria/fermented food production), *Oleomonas* (acetic bacteria/fermented food production), *Paracraurococcus* (acetic bacteria/fermented food production), *Rhodopila* (acetic bacteria/fermented food production), *Roseccoccus* (acetic bacteria/fermented food production), *Rubritepida* (acetic bacteria/fermented food production), *Saccharibacter* (acetic bacteria/fermented food production), *Stella* (acetic bacteria/fermented food production), *Swaminathania* (acetic bacteria/fermented food production), *Teichococcus* (acetic bacteria/fermented food production), *Zavarzinia* (acetic bacteria/fermented food production), *Pseudomonas* (*Pseudomonas* bacteria/beef, egg, meat, fish, vegetable), *Achromobacter* (*Achromobacter* bacteria/fish, meat), *Bacillus* (*Bacillus* bacteria/rice, vegetable), *Methanoculleus* (methane-producing bacteria/methane-producing bacterium parasitizing on animal intestines), *Methanosarcina* (methane-producing bacteria/methane-producing bacterium parasitizing on animal intestines), *Clostridium* (*Clostridium* bacteria/meat, milk, vegetable, canned food), *Micrococcus* (Actinomycetes/meat, fish), *Flavobacterium* (*Bacteroides* bacteria/putrefactive bacterium of food), *Pantoea, Acetobacter, Zymomonas, Xanthomonas*, and *Enterobacter*. These are assured to be safe to the living body because these are contained in many food items, or used in the course of producing food items.

Among these, at least one selected from the group consisting of *Serratia, Leclercia, Rahnella, Acidicaldus, Acidiphilium, Acidisphaera Acidocella, Acidomonas, Asaia, Belnapia, Craurococcus, Gluconacetobacter, Gluconobacter, Kozakia, Leahibacter, Muricoccus, Neoasaia Oleomonas, Paracraurococcus, Rhodopila, Roseococcus, Rubritepida, Saccharibacter, Stella, Swaminathania Teichococcus, Zavarzinia, Pantoea, Acetobacter, Zymomonas, Xanthomonas*, and *Enterobacter* is preferred.

More preferably, the gram negative bacterium is at least one selected from the group consisting of *Pantoea, Acetobacter, Zymomonas, Xanthomonas*, and *Enterobacter*. In particular, a lipopolysaccharide derived from *Pantoea* is currently used as a health food, and is particularly effective when it is orally administered. Extracts derived from these bacteria or modified substances thereof can also be used as they are.

When a lipopolysaccharide derived from the gram-negative bacterium or a salt thereof is used, it is generally necessary to take the safety in a living body into account, and a modified substance may be used to detoxify the same.

As the toll-like receptor 4 (TLR4) agonist, a derivative of the aforementioned specific lipopolysaccharide, for example, lipid A from which a polysaccharide moiety is removed, monophosphoryl lipid A, 3-deacylated MPL, or the like may be recited. Alternatively, the agonist may be a salt.

The lipid A from which a polysaccharide moiety of the lipopolysaccharide is removed can be an isolate derived from the specific gram-negative bacterium, or can be a synthetic product having the same structure as the isolate derived from the gram-negative bacterium.

As the modified substance of the lipid A, monophosphoryl lipid (MPL) obtained by dephosphorylation or a salt thereof is preferably used. The monophosphoryl lipid used herein may be monophosphoryl lipid itself, and a derivative thereof as long as the property of the monophosphoryl lipid is possessed. In particular, 3-deacylated monophosphoryl lipid (3D-MPL) that has already been proven as an immunostimulant in medical use, or synthetic glucopyranosyl lipid that is not deacylated, proposed in US Patent Application Publication No. 2010/0310602 is preferred from the viewpoint of safety in a living body.

Also, as the monophosphoryl lipid, the one derived from *Salmonella typhimurium* which is safe and has been used in the past is preferably used.

As the immunostimulant used in the present invention, an LPS derived from *Pantoea agglomerans* is more preferred. Among others, preferred is an LPS derived from *Pantoea agglomerans* having a molecular weight determined by SDS-PAGE using protein markers of 5000±3000 (2000 to 8000), preferably 5000±2000 (3000 to 7000). The molecular weight as used herein is measured by the position of the stained band by SDS-PAGE using protein markers, and the details will be described later.

The LPS derived from *Pantoea agglomerans* as used herein is a lipopolysaccharide in which the O-antigen moiety is formed of a repeating structure of rhamnose and glucose.

The LPS derived from *Pantoea agglomerans* can be produced by culturing *Pantoea agglomerans* by an ordinary method, collecting the bacterial cells from the culture medium, and purifying the collected bacterial cells according to a known method.

The molecular weight of the LPS derived from *Pantoea agglomerans* can be measured by the following method.

That is, for an LPS derived from *Pantoea agglomerans* prepared as a blend, or for an LPS derived from *Pantoea agglomerans* extracted and purified from a vaccine composition by an appropriate method, the molecular weight can be determined in the following manner.

An LPS derived from *Pantoea agglomerans* is dissolved in distilled water to prepare a 1 mg/mL solution, and the solution and Sample buffer solution 2ME+(Wako Pure Chemical Industries, Ltd.) are mixed in equal amounts. The resulting mixture is dipped in a boiling water bath for 5 minutes, and then immediately dipped in ice water to be rapidly cooled.

A slab gel electrophoresis tank (available from Marisol) is filled with a running buffer (available from ATTO), and 20% polyacrylamide gel is fixed in the electrophoresis tank. An amount of 10 μL of a sample is put into each sample groove, and electrophoresis is continued for at least one hour at a voltage of 100 V until the pigment is eluted from the gel. After completing the electrophoresis, silver staining is conducted with a silver staining kit 161-0443 (Bio-Rad Laboratories, Inc.) at room temperature, and the behavior is checked.

In the vaccine pharmaceutical composition for transdermal administration of the present invention, the ratio of the mass of the immunostimulant to the mass of the vaccine antigen of the vaccine pharmaceutical composition for transdermal administration of the present invention (total mass of the immunostimulant/total mass of the antigen) is preferably in the range of 0.002 to 500. If the ratio is less than 0.002, the function as a prophylactic or therapeutic agent for infectious diseases or cancer may be insufficient. If the ratio is more than 500, a safety problem may arise. The lower limit of the ratio is more preferably 0.01, and the upper limit thereof is more preferably 100.

In the vaccine pharmaceutical composition for transdermal administration of the present invention, the immunostimulant may be combined with other conventionally known immunostimulant(s) as long as a specific lipopolysaccharide derived from a gram-negative bacterium or a salt thereof is contained.

The vaccine pharmaceutical composition for transdermal administration of the present invention can be prepared by blending the aforementioned antigen and the immunostimulant with other ingredients (e.g., phosphate buffer solution) as needed, and stirring and mixing them by a known method, and further performing heating, cooling, or drying without heating as needed by a known method.

The vaccine pharmaceutical composition for transdermal administration of the present invention is used for inducing humoral immunity.

The humoral immunity-inducing effect may be quantitatively determined by any method. Various methods have been developed. For example, the effect can be determined by an immunity induction test using an animal model for immunological evaluation and ELISA (antigen-specific IgG antibody). The sample for determining humoral immunity may be, for example, blood of the animal model for immunological evaluation.

As used herein, the term "subject" means any animal to which the vaccine pharmaceutical composition at a practical stage can be administered so as to induce an immune response. The term typically means mammals including human (e.g., mouse, rat, canine, feline, leporine, equine, bovine, ovine, porcine, caprine, simian, and chimpanzee). The subject is particularly preferably a human.

<Vaccine Pharmaceutical Composition for Transdermal Administration>

The dosage form of the vaccine pharmaceutical composition for transdermal administration may be a solution for external application such as a liniment or a lotion; a spray for external application such as an aerosol; a gel; a patch such as a tape, or a poultice; an ointment, a plaster, or a cream. Categories, definitions, properties, production processes, and the like of these formulations are well known in the relevant art. For example, see the Japanese Pharmacopoeia, 16th Edition. Any known material may be used for these formulations.

The amounts of the antigen and the immunostimulant in the vaccine pharmaceutical composition for transdermal administration are not limited. The amount of the antigen is preferably 0.01% to 40% by weight, more preferably 0.1% to 30% by weight. The amount of the immunostimulant is preferably 0.001% to 40% by weight, more preferably 0.005% to 20% by weight.

The tape preferably includes an adhesive layer containing ingredients (i.e., the antigen, the immunostimulant, and the like), and a support that supports the adhesive layer. The tape may further include a release liner that prevents exposure of the adhesive layer before use and that can be easily removed from the adhesive layer at the time of use.

Any adhesive may be used to form the adhesive layer. Preferred is a hydrophilic base such as sodium polyacrylate because diffusional release of the antigen is favorable.

The amount of the adhesive in the adhesive layer is not limited, and is preferably 10% to 90% by weight, more preferably 20% to 80% by weight in terms of solids based on the total weight of the adhesive layer.

The amounts of the antigen and the immunostimulant in the adhesive layer are not limited. The amount of the antigen is preferably 0.01% to 40% by weight, more preferably 0.1% to 30% by weight. The amount of the immunostimulant is preferably 0.001% to 30% by weight, more preferably 0.01% to 20% by weight.

The adhesive layer may have any thickness. Preferably, the thickness is 10 to 1000 μm. With the thickness within the above range, the adhesive layer can readily contain the ingredients each in an effective amount and exhibit sufficient adhesion. Moreover, the adhesive layer with such a thickness can be readily formed.

The support is not limited, and is preferably one substantially impermeable to the above ingredients. In other words, it is preferably one that prevents a decrease in the amount of the antigen, the immunostimulant, and optionally the stimulant contained in the adhesive layer by not allowing them to pass through the support and escape from the back side.

Advantageous Effects of Invention

Allowing the noninvasive administration to the body surface, the vaccine pharmaceutical composition for transdermal administration of the present invention contributes to excellent compliance based on the following factors. Specifically, noninvasive administration (e.g., transdermal administration or transmucosal administration) or minimally invasive administration (e.g., administration to the skin surface after corneum exfoliation such as tape stripping, corneum perforation such as micro needling or electroporation) are allowed; patients are free from pain or fear of injections; patients can perform administration by themselves as the administration is easy; medical professionals can avoid a risk of infection due to needle pricking; in a case where repetitive administration is needed, the ambulatory frequency can be reduced to contribute to the improvement in quality of life of the patient; and medical wastes (e.g., needles) which necessitate special disposition are not generated.

In the case of the vaccine pharmaceutical composition of the present invention in the form of a patch such as a tape or a poultice, it is advantageous in that a predetermined dose can be reliably administered; the drug release rate can be controlled at any rate; and the drug is prevented from being attached to a site other than the intended site. In addition, since a patch is easily detachable, it is advantageous in that patients can immediately discontinue administration on their own by removing the patch from the site of application when an adverse effect occurs, for example.

Containing the above-mentioned specific immunostimulant in combination with at least one antigen, the vaccine pharmaceutical composition for transdermal administration of the present invention can safely and effectively induce a systemic immune response by administration thereof to the skin. The humoral immunity-inducing effect is significantly improved compared to administration of the antigen alone.

DESCRIPTION OF EMBODIMENTS

The present invention is specifically described with reference to, but not limited to, the following examples.

Preparation of Solutions for Transdermal Administration

Solutions were prepared according to the formulations shown in Tables 1 and 2. Specifically, an antigen and a lipopolysaccharide that is an immunostimulant each in an amount as shown in Table 1 or 2 were blended, and 80 μL of a phosphate buffer (NACALAI TESQUE, INC.) was added thereto, thereby preparing a vaccine composition.

A laminate of four sheets of BEMCOT (area: 0.7 $cm^2$) were attached to an adhesive tape for fixation at a central portion, thereby preparing a complex base. The BEMCOT part of the obtained complex base was impregnated with the total amount of the solution, and the resulting complex base was used as an administration sample in an immunity test.

Preparation of Creams for Transdermal Administration

Creams were prepared according to the formulations shown in Tables 1 and 2. Specifically, an antigen and a lipopolysaccharide that is an immunostimulant each in an amount as shown in Table 1 or 2 were blended, a base material (base cream) was added thereto such that the amount of the resulting mixture became 4 mg, and the mixture was mixed to prepare a cream. The base cream used was prepared by mixing materials according to the formulation shown in Table 4. White Vaseline, sorbitan monostearate, isostearic acid, benzyl alcohol, stearyl alcohol, polysorbate 60, and concentrated glycerin were purchased from Wako Pure Chemical Industries, Ltd. Cetanol was purchased from Tokyo Chemical Industry Co., Ltd.

A PET film/PET nonwoven fabric laminate (area: 0.7 $cm^2$) was attached to an adhesive tape for fixation at a central portion in such a manner that the PET film was in contact with the tape, thereby preparing a complex base. To the nonwoven fabric part of the obtained complex base was applied 4 mg of each cream. The resulting product was used as an administration sample in an immunity test.

Preparation of Tapes for Transdermal Administration

Tapes were prepared according to the formulations shown in Tables 1, 2, and 3. Specifically, an antigen, a lipopolysaccharide that is an immunostimulant, sodium polyacrylate as a base material, and water as a solvent each in an amount per $cm^2$ as shown in Table 1, 2, or 3 were mixed, and applied to a polyester release film in such a manner that the dried adhesive layer had a thickness of 100 μm, followed by drying to remove the moisture therein. To the resulting product was attached a polyester film as a support. A 1-$cm^2$ piece was punched from the resulting product, and a release film was removed therefrom. Thus obtained piece was evaluated as a tape for transdermal administration in an immunity test.

(Antigen)

OVA (Sigma-Aldrich Co. LLC) and an influenza vaccine antigen-containing solution H1N1 (A/California/07/2009, The Research Foundation for Microbial Diseases of Osaka University) were used.

Alternatively, also used were H3N2 (A/Victoria361/2011, The Research Foundation for Microbial Diseases of Osaka University), Influenza B virus (B/Wisconsin/1/2010, The Research Foundation for Microbial Diseases of Osaka University), Influenza B virus (B/Brisbane/60/2008, The Research Foundation for Microbial Diseases of Osaka University), a pneumococcal capsular polysaccharide-containing solution (Pneumovax NP, MSD K.K.), a HPV16 recombinant protein-containing solution (HPV16, ProSpec), a live attenuated rotavirus-containing solution (RotaTeq Oral Solution, MSD K.K.), an inactivated polio virus-containing solution (IMOVAX POLIO for subcutaneous injection, Sanofi), an inactivated hepatitis A virus-containing solution (Aimmugen, The Chemo-Sero-Therapeutic Research Institute), an inactivated Japanese encephalitis virus-containing solution (Encevac for subcutaneous injection, The Chemo-Sero-Therapeutic Research Institute), a live attenuated mumps virus-containing solution (live mumps vaccine, Kitasato Daiichi Sankyo Vaccine Co., Ltd.), a live attenuated measles virus-containing solution (live measles vaccine, Kitasato Daiichi Sankyo Vaccine Co., Ltd.), a live attenuated rubella virus-containing solution (dried live attenuated rubella vaccine, Kitasato Daiichi Sankyo Vaccine Co., Ltd.), a solution containing *haemophilus influenzae* type b polysaccharide-tetanus toxoid conjugate (ActHIB, Sanofi), a recombinant HBs antigen protein-containing solution (Bimmugen, The Chemo-Sero-Therapeutic Research Institute), a live attenuated yellow fever virus-containing solution (yellow fever vaccine, Sanofi), a tetanus toxoid-containing solution (tetanus toxoid, Denka Seiken Co., Ltd.), a live attenuated varicella virus-containing solution (dried live attenuated varicella vaccine, The Research Foundation for Microbial Diseases of Osaka University), a live BCG-containing solution (dried BCG vaccine, Japan BCG Laboratory), and an inactivated rabies virus-containing solution (tissue-cultured inactivated rabies vaccine, The Chemo-Sero-Therapeutic Research Institute).

(Immunostimulant)

A *Pantoea agglomerans*-derived lipopolysaccharide (NACALAI TESQUE, INC.) was used.

Alternatively, also used were an *Acetobacter* bacterium-derived lipopolysaccharide, a *Zymomonas* bacterium-derived lipopolysaccharide, and a *Xanthomonas* bacterium-derived lipopolysaccharide.

animal model for evaluating the humoral immunity induction level of the vaccine pharmaceutical composition for transdermal administration.

The animal model for immunological evaluation used was an animal in which the induction of humoral immunity by the antigen in the solutions, creams, and tapes for transdermal administration can be evaluated, in view of the compatibility of the antigen in the solutions, creams, and tapes for transdermal administration with MHC class 1 molecules of the animal.

Mouse Immunity Test of Preparations for Transdermal Administration

With the preparations for transdermal administration prepared as described above, a mouse immunity test using an animal model for immunological evaluation was performed. The right back of a mouse (C57BL6 NCr mouse, female, 7 weeks old) was shaved in advance. After a rearing period for recovery from the skin damage caused by the shaving, each preparation was administered to the skin of the right back of the mouse. The left back of the mouse was shaved at the same time. Twenty-four hours later, the preparation was removed. One week after the administration, the preparation was similarly administered to the skin of the left back of the mouse and removed 24 hours later.

One week after the second administration, the mouse serum was taken, and the antigen-specific IgG antibody titer in the serum was determined by ELISA.

TABLE 1

| No. | Dosage form | Antigen Name | Antigen Amount [ug] | Immunostimulant Name | Immunostimulant Amount [ug] | Skin condition | IgG antibody titer [Log2 titer] |
|---|---|---|---|---|---|---|---|
| Comparative Example 1 | Cream | OVA antigen [model antigen] | 200 | — | — | Normal | 7.3 |
| Example 1 | Cream | OVA antigen [mode; antigen] | 200 | *Pantoea* bacterium-derived LPS | 40 | Normal | 11.1 |
| Comparative Example 2 | Tape | OVA antigen [model antigen] | 200 | — | — | Normal | 7.2 |
| Example 2 | Tape | OVA antigen [model antigen] | 200 | *Pantoea* bacterium-derived LPS | 40 | Normal | 14.1 |
| Comparative Example 3 | Solution | A/California/07/2009 [H1N1] | 50 | — | — | Normal | 7.0 |
| Example 3 | Solution | A/California/07/2009 [H1N1] | 50 | *Pantoea* bacterium-derived LPS | 10 | Normal | 8.7 |
| Comparative Example 4 | Tape | A/California/07/2009 [H1N1] | 50 | — | — | Normal | 7.1 |
| Example 4 | Tape | A/California/07/2009 [H1N1] | 50 | *Pantoea* bacterium-derived LPS | 10 | Normal | 14.0 |
| Comparative Example 5 | Tape | B/Brisbane/60/2008 | 50 | — | — | Normal | 6.9 |
| Example 5 | Tape | B/Brisbane/60/2008 | 50 | *Pantoea* bacterium-derived LPS | 10 | Normal | 14.1 |

<Evaluation>

The solutions, creams, and tapes for transdermal administration obtained in the examples and comparative examples were evaluated for the following parameters.

(Evaluation of Humoral Immunity-inducing Effect)

A mouse immunity test using the solutions, creams, and tapes for transdermal administration was performed on animal models for immunological evaluation according to the following procedure. Then, the skin condition after administration of the preparation for transdermal administration was evaluated. Regarding Comparative Examples 1 to 5 and Examples 1 to 5, the antigen-specific humoral immunity induction level was evaluated by ELISA.

(Animal Model for Immunological Evaluation)

The "animal model for immunological evaluation" as used herein means an animal model for evaluating immunity induction properties of a vaccine pharmaceutical composition (the solutions, creams, and tapes for transdermal administration in the present case). Specifically, the term means an The evaluation of the humoral immunity-inducing effect shows that transdermal administration of the preparation for transdermal administration containing an immunostimulant (Examples 1 to 5) can provide a higher antigen-specific IgG antibody titer than administration of the solutions for transdermal administration containing no immunostimulant (Comparative Examples 1 to 5).

Accordingly, also when antigens such as those shown in Tables 2 and 3 below are used, the use of an immunostimulant according to the present invention leads to a high antigen-specific IgG antibody titer.

Tapes for transdermal administration were prepared according to the formulations shown in Table 5 in the same manner as the tapes for transdermal administration of Table 1. The right back of a mouse (C57BL6 NCr mouse, female, 7 weeks old) was shaved, and after the skin was subjected to a corneum exfoliation five times with an OPP tape (EZ Dunplon No. 3301EZ, Nitto Denko Corporation), each of the tape was administered to the skin (minimally invasive administration). The left back was shaved at the same time.

Twenty-four hours later, the tape for transdermal administration on the right back was removed. One week after the administration, the skin of the left back of the mouse was subjected to a corneum exfoliation in the same manner as above, and the tape for transdermal administration was administered thereto. The tape was removed 24 hours later. One week after the second administration, the mouse serum was taken, and the antigen-specific IgG antibody titer in the mouse serum was determined by ELISA.

Also in this immunization by the minimally invasive administration, humoral immunity specific to the administered antigen can be induced.

TABLE 2

| | | Antigen | | Immunostimulant | | |
|---|---|---|---|---|---|---|
| No. | Dosage form | Name | Amount [ug] | Name | Amount [ug] | Skin condition |
| Comparative test example 1 | Solution | OVA antigen [model antigen] | 200 | — | — | Normal |
| Test example 1 | Solution | OVA antigen [model antigen] | 200 | *Pantoea* bacterium-derived LPS | 10 | Normal |
| Comparative test example 2 | Tape | OVA antigen [model antigen] | 100 | — | — | Corneum detachment |
| Test example 2 | Tape | OVA antigen [model antigen] | 100 | *Pantoea* bacterium-derived LPS | 10 | Corneum detachment |
| Comparative test example 3 | Cream | A/California/07/2009 [H1N1] | 50 | — | — | Normal |
| Test example 3 | Cream | A/California/07/2009 [H1N1] | 50 | *Pantoea* bacterium-derived LPS | 10 | Normal |
| Comparative test example 4 | Tape | A/California/07/2009 [H1N1] | 10 | — | — | Corneum detachment |
| Test example 4 | Tape | A/California/07/2009 [H1N1] | 10 | *Pantoea* bacterium-derived LPS | 1 | Corneum detachment |
| Comparative test example 5 | Tape | A/California/07/2009 [H1N1] | 50 | — | — | Normal |
| Test example 5 | Tape | A/California/07/2009 [H1N1] | | *Acetobacter* bacterium-derived LPS | 10 | Normal |
| Comparative test example 6 | Tape | A/California/07/2009 [H1N1] | 50 | — | — | Normal |
| Test example 6 | Tape | A/California/07/2009 [H1N1] | 50 | *Zymomonas* bacterium-derived LPS | 10 | Normal |
| Comparative test example 7 | Tape | A/California/07/2009 [H1N1] | 50 | — | — | Normal |
| Test example 7 | Tape | A/California/07/2009 [H1N1] | 50 | *Xanthomonas* bacterium-derived LPS | 10 | Normal |
| Comparative test example 8 | Solution | A/Victoria361/2011 [H3N2] | 50 | — | — | Normal |
| Test example 8 | Solution | A/Victoria361/2011 [H3N2] | 50 | *Pantoea* bacterium-derived LPS | 10 | Normal |
| Comparative test example 9 | Cream | A/Victoria361/2011 [H3N2] | 50 | — | — | Normal |
| Test example 9 | Cream | A/Victoria361/2011 [H3N2] | 50 | *Pantoea* bacterium-derived LPS | 10 | Normal |
| Comparative test example 10 | Tape | A/Victoria361/2011 [H3N2] | 50 | — | — | Normal |
| Test example 10 | Tape | A/Victoria361/2011 [H3N2] | 50 | *Pantoea* bacterium-derived LPS | 10 | Normal |
| Comparative test example 11 | Tape | A/Victoria361/2011 [H3N2] | 10 | — | — | Corneum detachment |
| Test example 11 | Tape | A/Victoria361/2011 [H3N2] | 10 | *Pantoea* bacterium-derived LPS | 10 | Corneum detachment |
| Comparative test example 12 | Solution | B/Wisconsin/1/2010 | 50 | — | — | Normal |
| Test example 12 | Solution | B/Wisconsin/1/2010 | 50 | *Pantoea* bacterium-derived LPS | 10 | Normal |
| Comparative test example 13 | Cream | B/Wisconsin/1/2010 | 50 | — | — | Normal |
| Test example 13 | Cream | B/Wisconsin/1/2010 | 50 | *Pantoea* bacterium-derived LPS | 10 | Normal |
| Comparative test example 14 | Tape | B/Wisconsin/1/2010 | 50 | — | — | Normal |
| Test example 14 | Tape | B/Wisconsin/1/2010 | 50 | *Pantoea* bacterium-derived LPS | 10 | Normal |
| Comparative test example 15 | Tape | B/Wisconsin/1/2010 | 10 | — | — | Corneum detachment |
| Test example 15 | Tape | B/Wisconsin/1/2010 | 10 | *Pantoea* bacterium-derived LPS | 10 | Corneum detachment |
| Comparative test example 16 | Solution | B/Brisbane/60/2008 | 50 | — | — | Normal |
| Test example 16 | Solution | B/Brisbane/60/2008 | 50 | *Pantoea* bacterium-derived LPS | 10 | Normal |
| Comparative test example 17 | Cream | B/Brisbane/60/2008 | 50 | — | — | Normal |
| Test example 17 | Cream | B/Brisbane/60/2008 | 50 | *Pantoea* bacterium-derived LPS | 10 | Normal |
| Comparative test example 18 | Tape | B/Brisbane/60/2008 | 10 | — | — | Corneum detachment |
| Test example 18 | Tape | B/Brisbane/60/2008 | 10 | *Pantoea* bacterium-derived LPS | 10 | Corneum detachment |

TABLE 3

| | | Antigen | | Immunostimulent | | |
|---|---|---|---|---|---|---|
| No. | Dosage form | Name | Amount [ug] | Name | Amount [ug] | Skin condition |
| Comparative test example 19 | Tape | Pneumococcal capsular polysaccharide Pneumovax NP | 20 | — | — | Normal |
| Example 19 | Tape | Pneumecoccal capsular polysaccharide Pneumovax NP | 20 | *Pantoea* bacterium-derived LPS | 10 | Normal |
| Comparative test example 20 | Tape | HPV16 recombinant protein | 10 | — | — | Normal |
| Example 20 | Tape | HPV16 recombinant protein | 10 | *Pantoea* bacterium-derived LPS | 10 | Normal |
| Comparative test example 21 | Tape | live attenuated rotavirus (RIX4414 strain) | Vaccine 100 uL equivalent | — | — | Normal |
| Example 21 | Tape | live attenuated rotavirus (RIX4414 strain) | Vaccine 100 uL equivalent | *Pantoea* bacterium-derived LPS | 10 | Normal |
| Comparative test example 22 | Tape | Inactivated polio virus (type 1, type 2, type 3) | Vaccine 100 uL equivalent | — | — | Normal |
| Example 22 | Tape | Inactivated polio virus (type 1, type 2, type 3) | Vaccine 100 uL equivalent | *Pantoea* bacterium-derived LPS | 10 | Normal |
| Comparative test example 23 | Tape | Inactivated hepatitis A virus | Vaccine 100 uL equivalent | — | — | Normal |
| Exampel 23 | Tape | Inactivated hepatitis A virus | Vaccine 100 uL equivalent | *Pantoea* bacterium-derived LPS | 10 | Normal |
| Comparative test example 24 | Tape | Inactivated Japanese encephalitis virus | Vaccine 100 uL equivalent | — | — | Normal |
| Exampel 24 | Tape | Inactivated Japanese encephalitis virus | Vaccine 100 uL equivalent | *Pantoea* bacterium-derived LPS | 10 | Normal |
| Comparative test example 25 | Tape | Live attenuated mumps virus | Vaccine 100 uL equivalent | — | — | Normal |
| Exampel 25 | Tape | Live attenuated mumps virus | Vaccine 100 uL equivalent | *Pantoea* bacterium-derived LPS | 10 | Normal |
| Comparative test example 26 | Tape | Live attenuated measles virus | Vaccine 100 uL equivalent | — | — | Normal |
| Example 26 | Tape | Live attenuated measles virus | Vaccine 100 uL equivalent | *Pantoea* bacterium-derived LPS | 10 | Normal |
| Comparative test example 27 | Tape | Live attenuated rubella virus | Vaccine 100 uL equivalent | — | — | Nennal |
| Example 27 | Tape | Live attenuated rubella virus | Vaccine 100 uL equivalent | *Pantoea* bacterium-derived LPS | 10 | Normal |
| Comparative test example 28 | Tape | Haemophilus influenzae type b polysaccharide-tetanus toxoid conjugate | Vaccine 100 uL equivalent | — | — | Normal |
| Exampel 28 | Tape | Haemophilus influenzae type b polysaccharide-tetanus toxoid conjugate | Vaccine 100 uL equivalent | *Pantoea* bacterium-derived LPS | 10 | Normal |
| Comparative test example 29 | Tape | Recombinant HBs antigen protein | Vaccine 100 uL equivalent | — | — | Normal |
| Exampel 29 | Tape | Recombinant HBs antigen protein | Vaccine 100 uL equivalent | *Pantoea* bacterium-derived LPS | 10 | Normal |
| Comparative test example 30 | Tape | Live attenuated yellow fever virus | Vaccine 100 uL equivalent | — | — | Normal |
| Exampel 30 | Tape | Live attenuated yellow fever virus | Vaccine 100 uL equivalent | *Pantoea* bacterium-derived LPS | 10 | Normal |
| Comparative test example 31 | Tape | Tetanus toxoid | Vaccine 100 uL equivalent | — | — | Normal |
| Exampel 31 | Tape | Tetanus toxoid | Vaccine 100 uL equivalent | *Pantoea* bacterium-derived LPS | 10 | Normal |
| Comparative test example 32 | Tape | Live attenuated varicella virus | Vaccine 100 uL equivalent | — | — | Normal |
| Exampel 32 | Tape | Live attenuated varicella virus | Vaccine 100 uL equivalent | *Pantoea* bacterium-derived LPS | 10 | Normal |
| Comparative test example 33 | Tape | Live BCG | Vaccine 30 uL equivalent | — | — | Normal |
| Exampel 33 | Tape | Live BCG | Vaccine 30 uL equivalent | *Pantoea* bacterium-derived LPS | 10 | Normal |
| Comparative test example 34 | Tape | Inactivated rabies virus | Vaccine 200 uL equivalent | — | — | Normal |
| Exampel 34 | Tape | Inactivated rabies virus | Vaccine 200 uL equivalent | *Pantoea* bacterium-derived LPS | 10 | Normal |

TABLE 4

| Additive | Amount [parts by weight] |
|---|---|
| White Vaseline | 60.7 |
| Sorbitan monostearate | 0.7 |
| Isostearic acid | 12 |
| Benzyl alcohol | 2.4 |
| Cetanol | 2.4 |
| Stearyl alcohol | 3.5 |
| Polysorbate 60 | 3.5 |
| Concentrated glycerin | 2.4 |
| Purified water | 12.4 |
| Total | 100 |

TABLE 5

| | | Antigen | | Immunostimulant | | |
|---|---|---|---|---|---|---|
| No. | Dosage form | Name | Amount [ug] | Name | Amount [ug] | Skin condition |
| Comparative test example 35 | Tape | Pneumococcal capsular polysaccaride Pneumovax NP | 20 | — | — | Corneum detachment |
| Example 35 | Tape | Pneumococcal capsular polysaccaride Pneumovax NP | 20 | *Pantoea* bacterium-derived LPS | 10 | Corneum detachment |
| Comparative test example 35 | Tape | HPV16 recombinant protein | 10 | — | — | Corneum detachment |
| Example 36 | Tape | HPV16 recombinant protein | 10 | *Pantoea* bacterium-derived LPS | 10 | Corneum detachment |
| Comparative test example 37 | Tape | live attenuated rotavirus (RIX4414 strain) | Vaccine 100 uL equivalent | — | — | Corneum detachment |
| Example 37 | Tape | live attenuated rotavirus (RIX4414 strain) | Vaccine 100 uL equivalent | *Pantoea* bacterium-derived LPS | 10 | Corneum detachment |
| Comparative test example 38 | Tape | Inactivated polio virus (type 1, type 2, type 3) | Vaccine 100 uL equivalent | — | — | Corneum detachment |
| Example 38 | Tape | Inactivated polio virus (type 1, type 2, type 3) | Vaccine 100 uL equivalent | *Pantoea* bacterium-derived LPS | 10 | Corneum detachment |
| Comparative test example 39 | Tape | Inactivated hepatitis A virus | Vaccine 100 uL equivalent | — | — | Corneum detachment |
| Example 39 | Tape | Inactivated hepatitis A virus | Vaccine 100 uL equivalent | *Pantoea* bacterium-derived LPS | 10 | Corneum detachment |
| Comparative test example 40 | Tape | Inactivated Japanese encephalitis virus | Vaccine 100 uL equivalent | — | — | Corneum detachment |
| Example 40 | Tape | Inactivated Japanese encephalitis virus | Vaccine 100 uL equivalent | *Pantoea* bacterium-derived LPS | 10 | Corneum detachment |
| Comparatve test example 41 | Tape | Live attenuated mumps virus | Vaccine 100 uL equivalent | — | — | Corneum detachment |
| Example 41 | Tape | Live attenuated mumps virus | Vaccine 100 uL equivalent | *Pantoea* bacterium-derived LPS | 10 | Corneum detachment |
| Comparative test example 42 | Tape | Live attenuated measles virus | Vaccine 100 uL equivalent | — | — | Corneum detachment |
| Example 42 | | Live attenuated measles virus | Vaccine 100 uL equivalent | *Pantoea* bacterium-derived LPS | 10 | Corneum detachment |
| Comparative test example 43 | Tape | Live attenuated rubella virus | Vaccine 100 uL equivalent | — | — | Corneum detachment |
| Example 43 | Tape | Live attenuated rubella virus | Vaccine 100 uL equivalent | *Pantoea* bacterium-derived LPS | 10 | Corneum detachment |
| Comparative test example 44 | Tape | *Haemophilus influenza* type b polysaccharide-tetanus toxoid conjugate | Vaccine 100 uL equivalent | — | — | Corneum detachment |
| Example 44 | Tape | *Haemophilus influenza* type b polysaccharide-tetanus toxoid conjugate | Vaccine 100 uL equivalent | *Pantoea* bacterium-derived LPS | | Corneum detachment |
| Comparative test example 45 | Tape | Recombinant HBs antigen protein | Vaccine 100 uL equivalent | — | — | Corneum detachment |
| Example 45 | Tape | Recombinant HBs antigen protein | Vaccine 100 uL equivalent | *Pantoea* bacterium-derived LPS | 10 | Corneum detachment |
| Comparative test example 46 | Tape | Live attenuated yellow fever virus | Vaccine 100 uL equivalent | — | — | Corneum detachment |

TABLE 5-continued

| | | Antigen | | Immunostimulant | | |
|---|---|---|---|---|---|---|
| No. | Dosage form | Name | Amount [ug] | Name | Amount [ug] | Skin condition |
| Example 46 | Tape | Live attenuated yellow fever virus | Vaccine 100 uL equivalent | *Pantoea* bacterium-derived LPS | 10 | Corneum detachment |
| Comparative test example 47 | Tape | Tetanus toxoid | Vaccine 100 uL equivalent | — | — | Corneum detachment |
| Example 47 | Tape | Tetanus toxoid | Vaccine 100 uL equivalent | *Pantoea* bacterium-derived LPS | 10 | Corneum detachment |
| Comparative test example 48 | Tape | Live attenuated varicella virus | Vaccine 100 uL equivalent | — | — | Corneum detachment |
| Example 48 | Tape | Live attenuated varicella virus | Vaccine 100 uL equivalent | *Pantoea* bacterium-derived LPS | 10 | Corneum detachment |
| Comparative test example 49 | Tape | Live BCG | Vaccine 30 uL equivalent | — | — | Corneum detachment |
| Example 49 | Tape | Live BCG | Vaccine 30 uL equivalent | *Pantoea* bacterium-derived LPS | 10 | Corneum detachment |
| Comparative test example 50 | Tape | Inactivated rabies virus | Vaccine 200 uL equivalent | — | — | Corneum detachment |
| Example 50 | Tape | Inactivated rabies virus | Vaccine 200 uL equivalent | *Pantoea* bacterium-derived LPS | 10 | Corneum detachment |

INDUSTRIAL APPLICABILITY

The vaccine pharmaceutical composition of the present invention is universally usable for inducing humoral immunity to various antigens, exerts high humoral immunity-inducing effect, and is suitably used for transdermal administration.

The invention claimed is:

1. A vaccine pharmaceutical composition for transdermal administration [to be administered to] a human or an animal, the vaccine pharmaceutical composition comprising: a lipopolysaccharide or its salt derived from at least one gram-negative bacterium selected from the group consisting of *Pantoea, Acetobacter, Zymomonas*, and *Xanthomonas*, as an immunostimulant; and at least one antigen, the vaccine pharmaceutical composition having a ratio of the total mass of the immunostimulant to the total mass of the antigen from 0.002:1 to 500:1.

2. The vaccine pharmaceutical composition for transdermal administration according to claim 1, structured and arranged as a dosage form of a patch.

3. The vaccine pharmaceutical composition for transdermal administration according to claim 2, wherein the patch includes a support and an adhesive layer containing an adhesive, and the adhesive contains a hydrophilic base material.

4. The vaccine pharmaceutical composition for transdermal administration according to claim 1, which is used for inducing humoral immunity.

5. The vaccine pharmaceutical composition for transdermal administration according to claim 1, which is used for treating an infectious disease.

6. The vaccine pharmaceutical composition for transdermal administration according to claim 1, which is used for treating cancer.

7. The vaccine pharmaceutical composition for transdermal administration according to claim 1, wherein the antigen is at least one of a pathogen-derived antigen and a cancer antigen.

8. A method for inducing humoral immunity comprising administering to the skin of a subject a vaccine pharmaceutical composition, the vaccine pharmaceutical composition comprising: an immunostimulant-effective amount of a lipopolysaccharide or its salt derived from at least one gram-negative bacterium selected from the group consisting of *Pantoea, Acetobacter, Zymomonas*, and *Xanthomonas*, and at least one antigen, the vaccine pharmaceutical composition having a ratio of the total mass of the immunostimulant to the total mass of the antigen from 0.002:1 to 500:1.

9. The method according to claim 8, comprising administering the vaccine pharmaceutical composition by a patch.

10. The method of claim 9, wherein the patch includes a support and an adhesive layer, the adhesive layer containing an adhesive, and the adhesive containing a hydrophilic base material.

11. The method according to claim 8, wherein the subject is a human at risk of infection with an infectious disease.

12. The method according to claim 8, wherein the subject is a human with cancer.

13. The method according to claim 8, wherein the antigen is at least one of a pathogen-derived antigen and a cancer antigen.

14. The method according to claim 8, wherein the administering induces humoral immunity in the subject.

15. The method according to claim 8, wherein the subject is a human at risk for developing cancer.

16. The method according to claim 8, wherein the administering reduces the likelihood of developing an infection disease.

17. The method according to claim 8, wherein the administering reduces the likelihood of developing cancer.

* * * * *